(12) United States Patent
Kostrzewski et al.

(10) Patent No.: US 12,070,286 B2
(45) Date of Patent: Aug. 27, 2024

(54) SYSTEM AND METHOD FOR LIGAMENT BALANCING WITH ROBOTIC ASSISTANCE

(71) Applicant: GLOBUS MEDICAL, INC., Audubon, PA (US)

(72) Inventors: Szymon Kostrzewski, Lausanne (CH); Olivier Chappuis, Lutry (CH)

(73) Assignee: Globus Medical, Inc, Audubon, PA (US)

( * ) Notice: Subject to any disclaimer, the term of this patent is extended or adjusted under 35 U.S.C. 154(b) by 298 days.

(21) Appl. No.: 17/568,310

(22) Filed: Jan. 4, 2022

(65) Prior Publication Data

US 2022/0218425 A1 Jul. 14, 2022

Related U.S. Application Data

(63) Continuation of application No. 17/568,050, filed on Jan. 4, 2022.
(Continued)

(51) Int. Cl.
| | |
|---|---|
| *A61B 34/32* | (2016.01) |
| *A61B 34/00* | (2016.01) |
| *A61B 34/10* | (2016.01) |
| *A61B 34/30* | (2016.01) |
| *A61B 90/00* | (2016.01) |
| *G16H 20/40* | (2018.01) |
| *G16H 40/63* | (2018.01) |

(52) U.S. Cl.
CPC .............. *A61B 34/32* (2016.02); *A61B 34/10* (2016.02); *A61B 34/30* (2016.02); *A61B 34/76* (2016.02); *A61B 90/06* (2016.02); *G16H 20/40* (2018.01); *G16H 40/63* (2018.01); *A61B 2034/104* (2016.02); *A61B 2034/105* (2016.02); *A61B 2034/108* (2016.02); *A61B 2090/066* (2016.02)

(58) Field of Classification Search
CPC ......... A61B 34/32; A61B 34/30; A61B 34/76; A61B 90/06; A61B 2034/104; A61B 2090/066; G16H 20/63
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| | (Continued) | |

OTHER PUBLICATIONS

US 8,231,638 B2, 07/2012, Swarup et al. (withdrawn)

*Primary Examiner* — Kevin T Truong
*Assistant Examiner* — Diana Jones

(57) ABSTRACT

A surgical robot system includes a surgical robot having a robot base and a robot arm connected to the robot base. The surgical robot system further includes a joint manipulation arm configured to be attached to the robot arm and to be connected to an appendage of a patient and moved to apply force and/or torque to a joint connecting the appendage through movement of the robot arm. The surgical robot system further includes force and/or torque sensor apparatus configured to output a feedback signal providing an indication of an amount of force and/or torque that is being applied to the robot arm and/or the joint manipulation arm. At least one controller is configured to determine ligaments balancing at the joint based on a plurality of measurements of the feedback signal, and to output information characterizing the ligaments balancing.

15 Claims, 11 Drawing Sheets

Related U.S. Application Data

(60) Provisional application No. 63/135,068, filed on Jan. 8, 2021.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |

(56) References Cited

U.S. PATENT DOCUMENTS

| | | |
|---|---|---|
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |

(56) References Cited

U.S. PATENT DOCUMENTS

| | | |
|---|---|---|
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,119,656 B2 * | 9/2015 | Bose ............... A61B 17/22 |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |

(56) References Cited

U.S. PATENT DOCUMENTS

| | | |
|---|---|---|
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |

(56) References Cited

U.S. PATENT DOCUMENTS

| | | |
|---|---|---|
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0278754 A1* | 9/2016 | Todorov .................. A61F 2/389 |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2017/0360512 A1* | 12/2017 | Couture .................. A61B 34/30 |
| 2018/0132949 A1* | 5/2018 | Merette .................. G06T 11/60 |

\* cited by examiner

SYSTEM AND METHOD FOR LIGAMENT BALANCING WITH ROBOTIC ASSISTANCE

CROSS-REFERENCE TO RELATED APPLICATIONS

This application is a continuation of U.S. patent application Ser. No. 17/568,050 filed on Jan. 4, 2022, which claims the benefit of U.S. Provisional Patent Application Ser. No. 63/135,068, filed on Jan. 8, 2021, the disclosure and content of which is incorporated by reference herein in its entirety.

FIELD

The present invention relates to robotic surgery and more particularly to ligament balancing in orthopedic surgery and knee arthroplasty with robotic assistance.

BACKGROUND

Ligaments are important in knee kinematics as together with bones they ensure knee stability. Ligaments also determine knee joint kinematics across the range of motion and provide additional functions like proprioception (sensory information about knee state).

In order to correctly plan the most appropriate implant position for a specific patient, a surgeon needs to consider how to maintain proper balance of a patient's knee ligaments. The balance procedure is performed intra-operatively, i.e., after opening patient knee. Usually, the surgeon will remove any osteophytes first in order to prevent them from interfering with ligaments assessment. Next, the surgeon will move the knee across the range of motion with no medio-lateral forces and then while applying the lateral varus and valgus forces to feel how the knee moves. The surgeons attempts to identify knee laxity, any irregularities, force required to move etc. The procedure provide initial information to consider during implant planning stage, such as how to adapt for this patient implant sizing and placement, target deformity correction, etc. After performing the necessary cuts and placing a trial implant, the surgeon will typically redo the ligaments balancing process to compare the present balancing to the initial balancing in view of a desired goal to be achieved. Similarly, after placing a final implant the surgeon may perform a final check of the ligaments balancing.

Limitations of existing processes to assess ligaments balancing can include the following:
- Subjectivity: the surgeon needs to perform the whole process using imprecise physically perceived functionalities. The surgeon assesses knee ligaments balancing by moving the leg with hands across the Range Of Motion (ROM) of the knee joint (changing flexion-extension angle between 0 and around 130 deg). Therefore, the ligaments balancing is a subjective and imprecise assessment process.
- The knowledge and skills of the surgeon are difficult to transfer to another surgeon as it is a matter of experience, including how and where the surgeon applies forces for leg movements, the intensity of the forces, subjective feeling and assessment, etc.
- The associated knowledge and skills are also difficult to transfer between patients as each patients has different ligament and skeletal structures which necessitate adapting of the processes by the surgeon.
- Preciseness of the processes depends on an individual surgeon's attentiveness, physical strength, tiredness, etc.

SUMMARY

Some embodiments of the present disclosure are directed to a surgical robot system that includes a surgical robot having a robot base and a robot arm connected to the robot base. The surgical robot system further includes a joint manipulation arm configured to be attached to the robot arm and to be connected to an appendage of a patient and moved to apply force and/or torque to a joint connecting the appendage through movement of the robot arm. The surgical robot system further includes a force and/or torque sensor apparatus configured to output a feedback signal providing an indication of an amount of force and/or torque that is being applied to the robot arm and/or the joint manipulation arm. At least one controller is configured to determine ligaments balancing at the joint based on a plurality of measurements of the feedback signal, and to output information characterizing the ligaments balancing.

Some other related embodiments are directed to a method by a surgical robot system which includes a surgical robot with a robot arm connected to move a join manipulation arm to apply force and/or torque to a joint connecting an appendage of a patient. The method includes obtaining, from a force and/or torque sensor apparatus, a feedback signal providing an indication of an amount of force and/or torque that is being applied to the robot arm and/or the joint manipulation arm. The method determines ligaments balancing at the joint based on a plurality of measurements of the feedback signal, and to output information characterizing the ligaments balancing.

Some other related embodiments are directed to a computer program product including a non-transitory computer readable medium storing program instructions executable by at least one processor of a surgical robot system including a surgical robot with a robot arm connected to move a join manipulation arm to apply force and/or torque to a joint connecting an appendage of a patient. The program instructions when executed by the at least one processor operate to obtain, from a force and/or torque sensor apparatus, a feedback signal providing an indication of an amount of force and/or torque that is being applied to the robot arm and/or the joint manipulation arm. The operations determine ligaments balancing at the joint based on a plurality of measurements of the feedback signal, and to output information characterizing the ligaments balancing.

Other surgical robot systems and corresponding methods and computer program products according to embodiments of the inventive subject matter will be or become apparent to one with skill in the art upon review of the following drawings and detailed description. It is intended that all such additional surgical robot systems, methods, and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
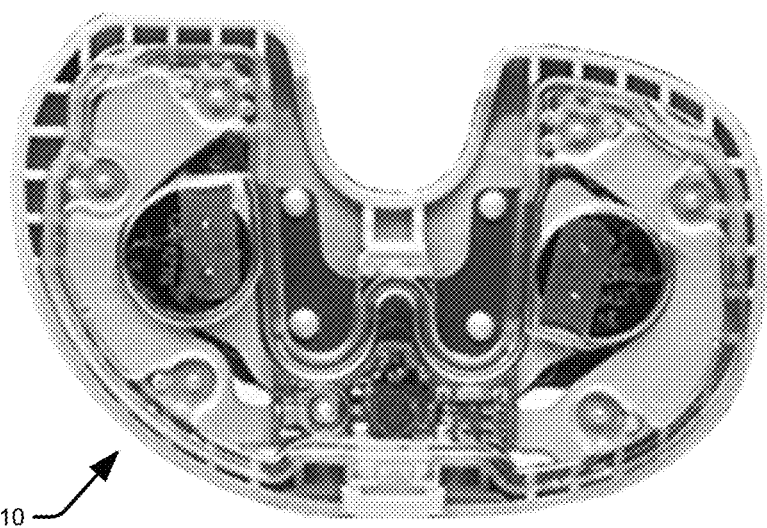
FIG. 1 illustrates an example VERASENSE sensor.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

This application incorporates by reference the entire content of U.S. patent application Ser. No. 15/157,444 filed May 18, 2016.

Some more advanced ligaments balancing assessment processes have been proposed, but are subject to various limitations. One sensor-assisted technology product is called VERASENSE from Orthosensor. VERASENSE is a sensor-assisted device used during primary and revision Total Knee Arthoplasty (TKA). This technology sends real-time data to a monitor in the operating room, which a surgeon can reference to make decisions about soft tissue balance and decide on customization of implant position for a particular patient.

Figure 2:
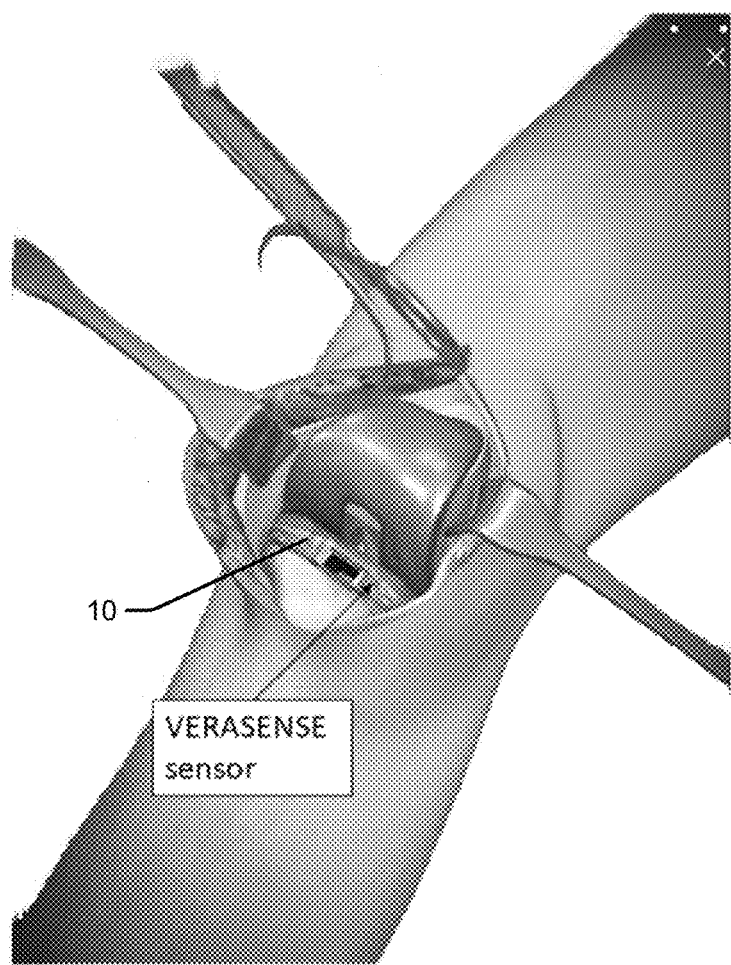
FIG. 2 illustrates the VERASENSE sensor of FIG. 1 inserted into a knee.

FIG. 1 illustrates an example VERASENSE sensor 10. FIG. 2 illustrates the VERASENSE sensor 10 inserted into a knee. One drawback of this device and process is that the surgeon is responsible for moving the leg across an estimated range of motion (ROM) of the knee to is responsible for applying levels of varus and/or valgus forces which decreases preciseness and repeatability of these procedures such as explained above. Moreover, there no common consensus of acceptance criteria for particular measured values and how the ligament balancing process should be adapted depending upon the measured values.

It is important for the ligament balancing process to be transferrable between patients while maintaining effectiveness of results. Navigation-based ligaments balancing can include measuring position of tibia and femur during a ROM test while a surgeon applies varus and valgus forces. With potentially additional information be provided by medical images (e.g. CT, segmented bone 3D models) and/or measurements (e.g. condylar/bone surface using a tracked pointer by a camera tracking system) useful measurements for assessing ligaments balancing can be identified. The measurements can include gap size, maximal and/or minimal varus and/or valgus angles, contact surfaces and points between bones, etc. In existing approaches the surgeon is entirely responsible for moving the leg across the estimated ROM which gives rise to the disadvantages described above.

Various embodiments of the present disclosure are directed to operating a surgical robot system to perform the ligaments balancing process. The surgical robot system is also referred to herein a "robot system" and "robot" for brevity. The robot system can be configured to precisely apply pre-defined constraints (forces and torques) on patient anatomy while measuring the resulting/reaction forces using, e.g., Force and/or Torque (FT) sensor apparatus(es). The robot system can precisely perform the ligaments balancing process in a manner that is repeatable with a particular patient and as a process that is repeatable across different patients.

Three separate example processes are now explained which may be performed by the robot system to carry out ligaments balancing and provide navigated assistance to a surgeon during a surgical procedure. The first process is referred to as Free Knee Motion through which the robot system operates to match measurements of initial knee ligaments balancing before and after implantation of an implant into a patient knee. The second process is referred to as Ligaments Characteristics Identifications through which the robot system operates to perform measurements of ligaments characteristics (e.g., elasticity, attachment points, etc.) when assisting a surgeon with choosing the best implant position, type and size for a specific patient. The third process is referred to as Standardized Measurement through which the robot system accesses a knowledge database defining standard "good" ligaments balancing to obtain baseline balancing measurements based on which the robot system performs operations after implantation to balance the specific patient's ligaments. These example processes can be used separately or together.

Although various embodiments are described and illustrated in the context of knee ligaments balancing, concepts implemented from these and other embodiments are not limited to the knee. These concepts may be used to evaluate and/or balance ligaments at other joints of the human body.

Figure 3:
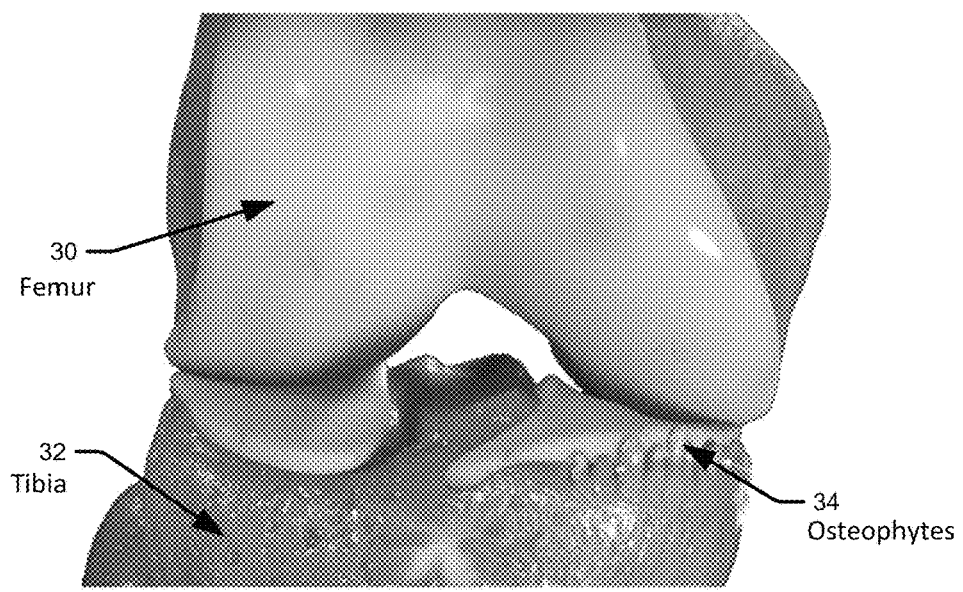
FIG. 3 illustrates a knee with exposed femur and tibia, and further illustrates osteophytes which formed on the tibia as an abnormal bony growth.

The Free Knee Motion process is explained in accordance with some embodiments. The robot system operates to determine how ligaments guide knee motion of a specific patient before implant placement and then closely match the ligament balancing to provide desired, e.g., substantially the same, knee motion after implant placement. For patients with advanced arthritis, osteophytes develop around knee joint. FIG. 3 illustrates a knee with exposed femur 30 and tibia 32, and further illustrates osteophytes 34 which formed on the tibia 32 as an abnormal bony growth. The osteophytes 34 negatively influence natural knee kinematics and can complicate the process for determining correct ligaments balance. In a surgical procedure, a small amount of bone including the osteophytes 34 is removed, which releases the tension inside the knee. The ligaments maintaining the knee joint are thereby relaxed.

Figure 4:
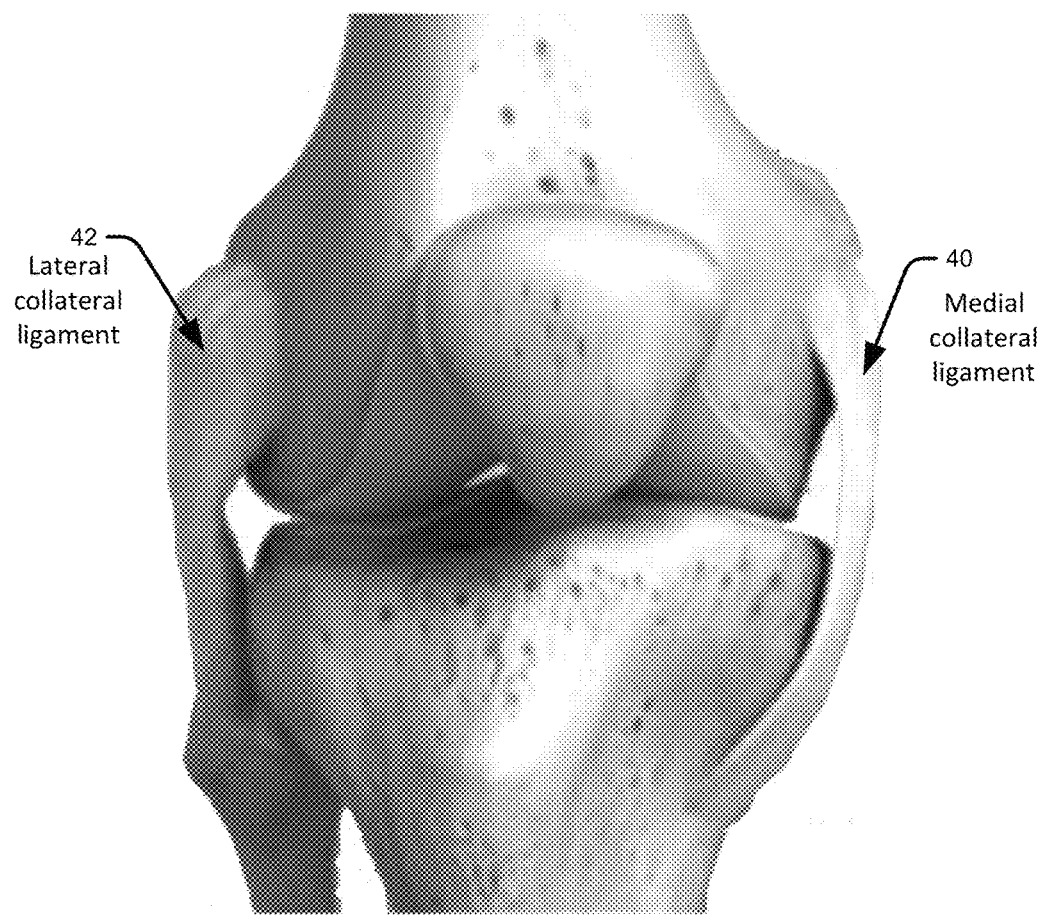
FIG. 4 illustrates a MCL and a LCL which extend between the femur and tibia.
Figure 5:
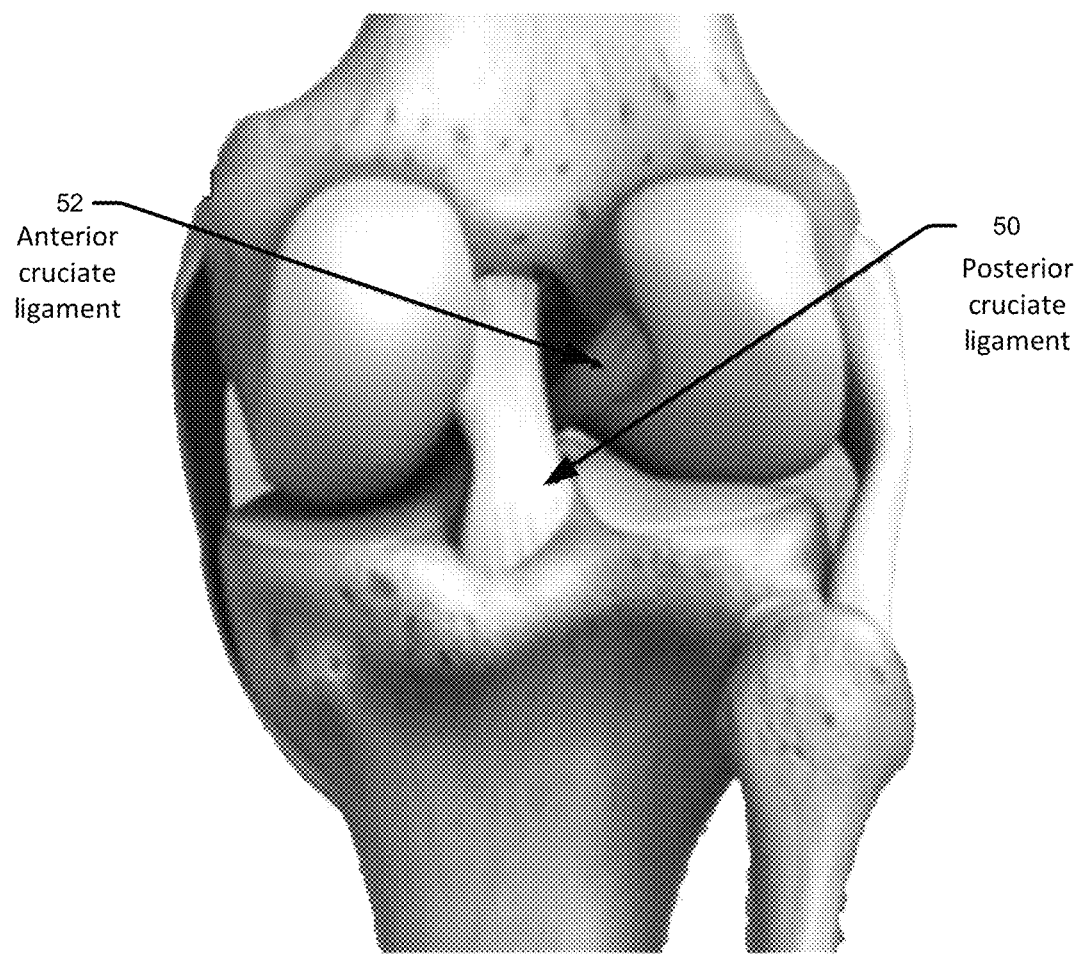
FIG. 5 illustrates a PCL and an ACL which extend between the femur and tibia.

There are four principal ligaments for correct knee balance (lower collateral ligament (LCL), medial collateral ligament (MCL), anterior cruciate ligament (ACL), and posterior cruciate ligament (PCL)), completed by other tissue in knee capsule, which are represented in the illustrations of knees in FIGS. 4 and 5. FIG. 4 illustrates a MCL 40 and a LCL 42, which extend between the femur and tibia. FIG. 5 illustrates a PCL 50 and an ACL 52, which extend between the femur and tibia.

Figure 6:
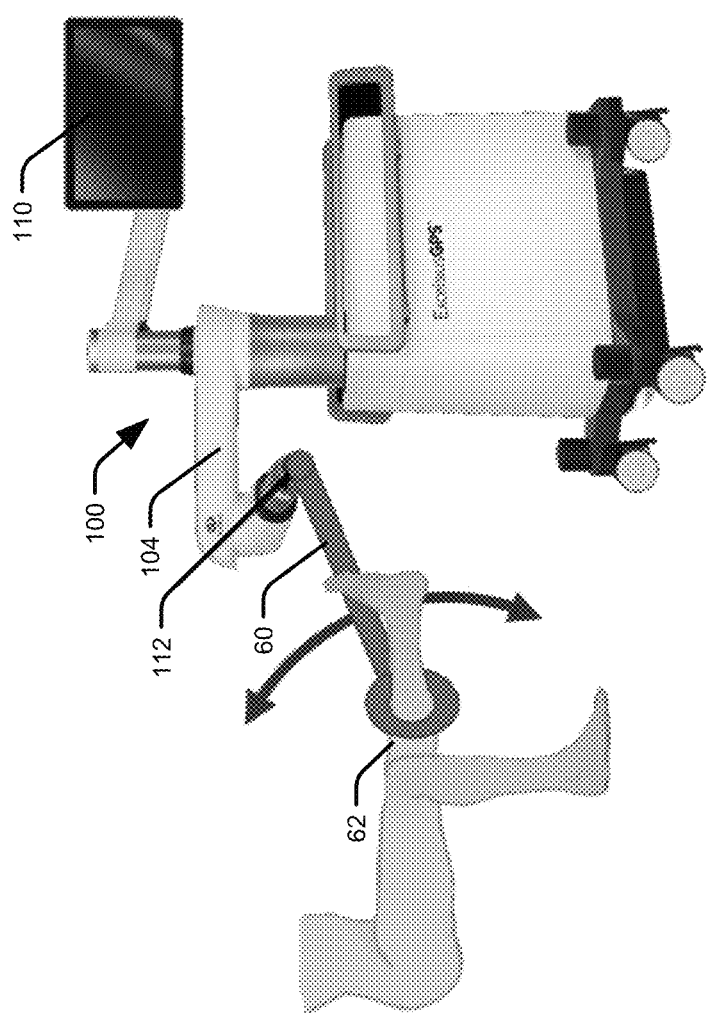
FIG. 6 illustrates a surgical robot system that includes a robotic arm with an end-effector attached to an knee manipulation arm and configured to operate in accordance with some embodiments of the present disclosure.

FIG. 6 illustrates a surgical robot system 100 that includes a robotic arm 104 with an end-effector 112. The end-effector can be releasably connected to a knee manipulation arm 60, which is illustrated as being connected to the lower leg 62 of a patient. The robot system 100 is configured to perform robot-assisted ligaments balancing. The robot system 100 may be based on an ExcelsiusGPS product from Globus Medical, and may be configured as disclosed in U.S. patent application Ser. No. 15/157,444 which is incorporated herein. Although the knee manipulation arm 60 is illustrated as being adapted to be connected to a leg, it may be adapted to connect to any appendage connected through ligaments to a joint of the body. Thus, the term "knee manipulation arm" is also referred to as a "joint manipulation arm." Thus, the end-effector 112 can be configured to connect to other types of joint manipulation arms.

The robotic arm 104 can be configured to move the patient's lower leg 62 through a defined ROM while performing measurements of force and/or torque applied to the knee manipulation arm 60. Alternatively or additionally the robotic arm 104 can be configured to perform measurements of force and/or torque applied to the knee manipulation arm 60 while a surgeon moves the patient's leg 62 through a ROM. The measurements can be performed by one or more force and/or torque sensor apparatus(es) in a distal end of the arm 104, such as within the end-effector 112, and/or in the knee manipulation arm 60 to measure force and/or torque at a joint of the arm 104. The force and/or torque sensor apparatus may directly measure force and/or torque at, e.g., a joint of the arm 104 and/or by measuring current applied to one or more motors which guide movement of the robotic arm 104.

Figure 14:
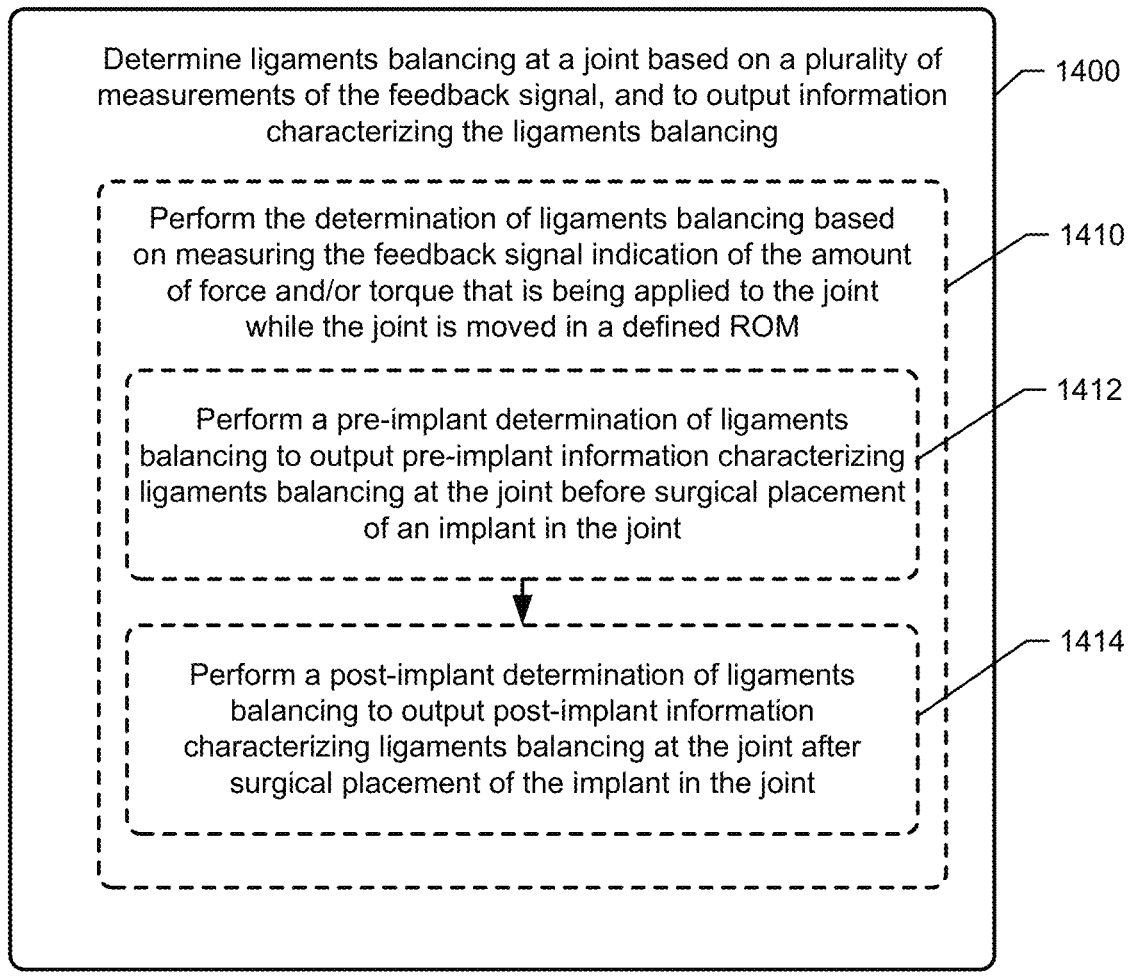
FIG. 14 illustrates operations performed by the at least one controller of the surgical robot system in accordance with some embodiments of the present disclosure.

FIG. 14 illustrates operations performed by the at least one controller of the robot system 100 in accordance with some embodiments of the present disclosure. Referring to FIGS. 6 and 14, the robot system 100 can include a joint manipulation arm (e.g., 60) configured to be attached to the robot arm 104 (e.g., to the end effector 112) and to be connected to an appendage of a patient (e.g., the leg 62 or other appendage) and moved to apply force and/or torque to a joint connecting the appendage through movement of the robot arm 104. The robot system 100 includes a force and/or torque sensor apparatus is configured to output a feedback signal providing an indication of an amount of force and/or torque that is being applied to the robot arm 104 and/or the joint manipulation arm. The robot system 100 includes at least one controller (e.g., surgical robot 102, computer platform 1600 in FIG. 16, etc.) that is configured to determine 1400 ligaments balancing at the joint based on a plurality of measurements of the feedback signal, and to output information characterizing the ligaments balancing.

The knee manipulation arm 60 can be configured to be attached to the lower leg 62 in a way that enables the robotic arm 104 to move the lower leg 62 while measuring the reaction forces and/or torques. Operations by the robot system 100 to perform ligaments balancing can be performed as the same point in the surgery as the manual ligaments balancing or may be performed more often such as responsive to any one or more of the following: before a surgical procedure to open the knee; after opening the knee; after a surgical procedure to remove osteophyte; after each cut on the knee; before and/or after performing a trial implant placement in the knee; and before and/or after performing a final implant placement in the knee. The robot system 100 can be configured to use the measurements to provide information guidance to the surgeon to assist with selection of implant size for the patient, placement of an implant into the knee of the patient (e.g. medio-lateral for femoral component, positioning and rotation of tibial component, size of polyethylene etc.), etc.

In the example embodiment of FIG. 14, the at least one controller can perform 1410 the determination 1400 of ligaments balancing to output the information characterizing ligaments balancing at the joint, based on repeated measurements of the feedback signal indication of the amount of force and/or torque while the joint is moved in a defined range of motion (ROM).

In a further embodiment, the joint manipulation arm is configures as a knee manipulation arm 60 adapted to be attached to the robot arm and to be connected to the leg 62 of the patient to apply force and/or torque to a knee of the leg 62 through movement of the robot arm 104. The force and/or torque sensor apparatus is configured to output a feedback signal providing an indication of an amount of force and/or torque that is being applied to the knee. The at least one controller is configured to determine ligaments balancing at the knee based on the plurality of measurements of the feedback signal, and to output information characterizing the ligaments balancing.

Also in the example embodiment of FIG. 14, the at least one controller can perform 1410 the determination 1400 of ligaments balancing through operations that include performing a pre-implant determination 1412 of ligaments balancing to output pre-implant information characterizing ligaments balancing at the joint before surgical placement of an implant in the joint, and performing a post-implant determination 1414 of ligaments balancing to output post-implant information characterizing ligaments balancing at the joint after surgical placement of the implant in the joint.

In a further embodiment, the at least one controller is further configured to display to an operator an indication of the defined ROM that the joint needs to be moved through during the pre-implant determination of ligaments, and to display to the operator a further indication of a present tracked location of the joint being moved by the operator and/or by the surgical robot in the defined ROM.

During robot-assisted ligaments balancing, the robot system 100 is configured to perform operations that move the knee manipulation arm 60 via the arm 104 to cause predefined movements of the lower leg 62 within the knee ROM and which may be performed to cause defined levels of resultant force and/or torque to be created at the sensor(s) of the arm 104 in order to measure the natural position given by the ligaments for the knee. One or more of the operations may include moving the lower leg 62 along a straight line without applying lateral forces and repeating the same movement when applying varus and/or valgus forces. The robot system 100 may be configured to operate in an impedance control mode through which it applies a substantially constant force and/or torque while performing the defined motion of the lower leg 62 and performing measurements of the natural position provided by the ligaments.

In some embodiments, the surgical robot further comprises at least one motor operatively connected to move the robot arm 104 relative to the robot base. The at least one controller is further configured to perform the determination 1400 of ligaments balancing based on controlling the at least one motor to move the robot arm 104 along a path computed to move the joint in the defined ROM while repetitively performing the measurements of the feedback signal indicating the amount of force and/or torque that is being applied to the joint.

In a further embodiment, the at least one controller is further configured to perform the determination 1400 of ligaments balancing based on controlling the at least one motor to move the robot arm 104 to cause the joint to move in the defined ROM without lateral forces being applied to the knee and while performing a first set of measurements of the feedback signal indicating the amount of force and/or torque that is being applied to the joint, and to control the at least one motor to move the robot arm 104 and cause the joint in the defined ROM with defined lateral forces being applied to the knee and while performing a second set of measurements of the feedback signal indicating the amount of force and/or torque that is being applied to the joint. The at least one controller is further configured to determine the ligaments balancing based on a combination of the first and second sets of measurements.

The robot system 100 can be configured to operate to determine the size of gaps between bones (e.g. medial and lateral gap between tibia and femur), ligaments mechanical characteristics (e.g. flexibility, attachment points, health state) and other ligaments balance related parameters as a function of knee flexion angle and/or for a ROM, based on using the measurements of reaction forces and/or torque and optionally further based on positions of the robotic arm 104 and/or end-effector 112, positions of the tibia and the femur which can be tracked using a tracking camera as disclosed in U.S. patent application Ser. No. 16/587,203, filed Sep. 30, 2019, (incorporated herein by reference), and/or defined system set-up for tibia and femur measurements.

The determined information can be presented to a surgeon or other user via a display device (e.g., display screen 110, head-mounted display (HMD) 150, etc.) to provide computer assistance for implant selection, implant placement, and/or assessment of estimated surgical procedure outcomes. Software of the robot system 100 may operate to use the determined information to recommend to the surgeon an implant type, size, and placement for the particular patient. The software may operate using defined optimization criteria which estimates measurements that would result after a particular implant placement configuration and operate to try adapting the implant type, size, and/or placement to more precisely match the resulting measurement to the initially acquired set of measurements, i.e., before surgical steps that affect the ligaments balance, and/or a define set of measurements where a surgeons seeks to achieve resulting measurements that differ from the initially acquired set of measurements. The software may operate using a machine decision process which is based on one or more of a rule based decision process, artificial intelligence process, neural network circuit, etc. In some embodiments, the computer assistance can result in the structure of the knee after implant placement closely matching the original or other desired knee structure, and thus improve patient feeling and potentially outcomes from the surgical procedure.

In the example embodiment of FIG. 14, the at least one controller can perform 1410 the determination 1400 of ligaments balancing to generate the outputted information which characterizes mechanical properties of the ligaments and/or points where the ligaments attach to one or more bones. For example, the at least one controller may display indicia indicating ligament attachment points on a displayed medical image of the joint, such shown by the attachment point indicia 80 in FIG. 8.

Various specific movements that can be performed with assistance from the robot system 100 are now discussed with reference to FIGS. 7 to 13.

Figure 7:
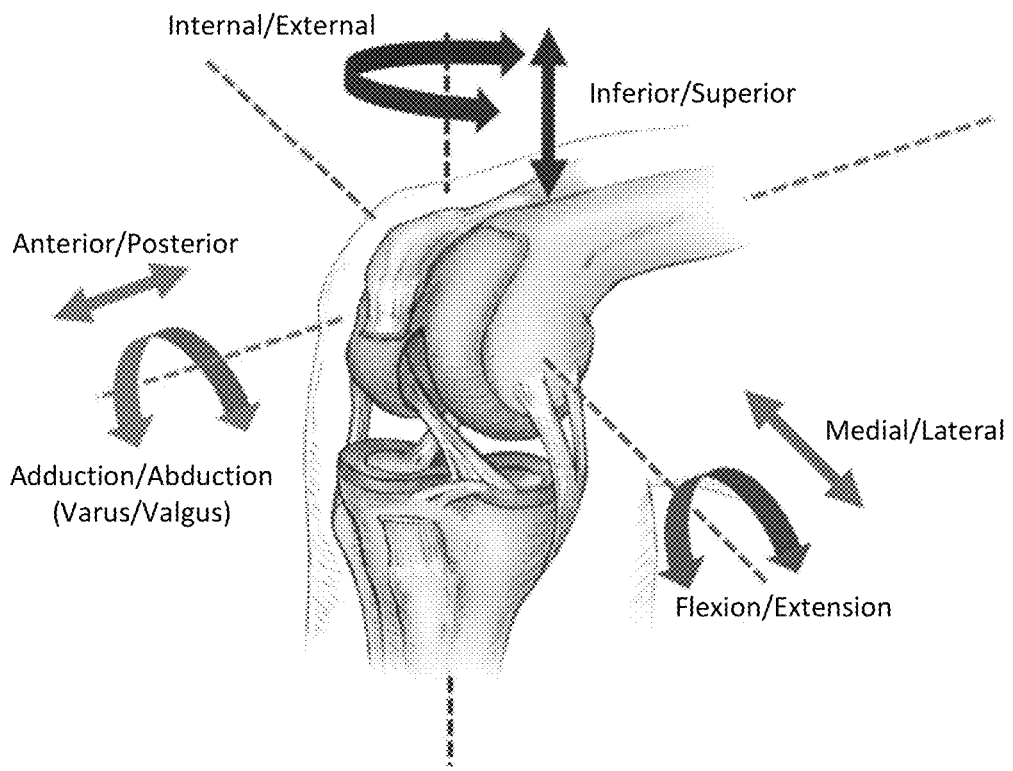
FIG. 7 illustrates different defined movements over degrees of freedom in the knee joint which may be performed by the robot system while measuring force and/or torque in accordance with some embodiments of the present disclosure.

In some embodiments, the robot system 100 operates to measure the knee laxity across a ROM using specifically defined robot movements, e.g., of the knee manipulation arm 60. FIG. 7 illustrates different defined movements over degrees of freedom in the knee joint which may be performed by the robot system 100 while measuring force and/or torque. In FIG. 7, the circular arrows (rotational movements) represent the torques applied to the knee and the linear arrows (linear movements) represent the forces applied to the knee and possible respective movements in response to these forces/torques. During computer assisted ligaments balancing, the robot system 100 can operate to perform specific movements of the lower leg 62 which may be one or any combination of the rotational and/or linear movements shown in FIG. 7 to calculate and/or identify, e.g., attachment points of the ligaments to bone and/or ligaments mechanical properties (e.g. stiffness, flexibility, elasticity).

Figure 8:
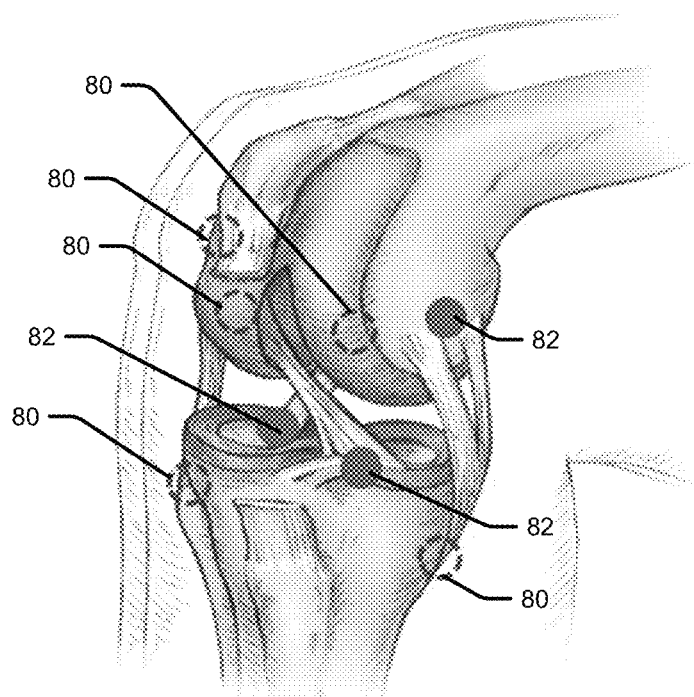
FIG. 8 illustrates example attachment points of ligaments to bone and computed locations of applied forces by the surgical robot system operating in accordance with some embodiments of the present disclosure.
Figure 9:
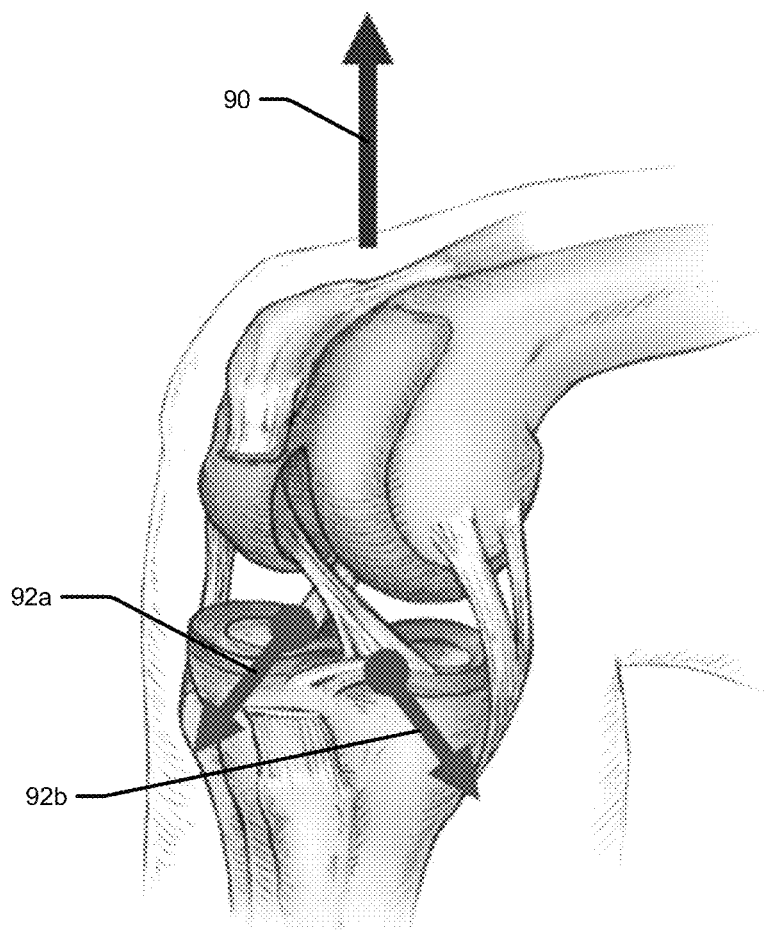
FIG. 9 illustrates a force vector applied by the surgical robot system to the knee and resultant reaction force vectors by the cruciate ligaments to keep the tibia and the femur attached to each other while the robotic arm is applying forces during a robot-assisted ligaments balancing process operating in accordance with some embodiments of the present disclosure.

FIG. 8 illustrates example attachment points 80 of ligaments to bone and computed locations of applied forces by the robot system 100 operating in accordance with some embodiments of the present disclosure. For example, the robot system 100 may operate to progressively move the lower leg 62 to measure force and/or torque on the knee within its ROM, and calculate locations 82 on the bones corresponding to the application of the force by each ligament, i.e., ligaments attachment locations. FIG. 9 illustrates a force vector 90 applied by the robot system 100 to the knee and resultant reaction force vectors 92a-92b by the cruciate ligaments to keep the tibia and the femur attached to each other while the robotic arm 104 is applying forces during a robot-assisted ligaments balancing process operating in accordance with some embodiments of the present disclosure.

Figure 10:
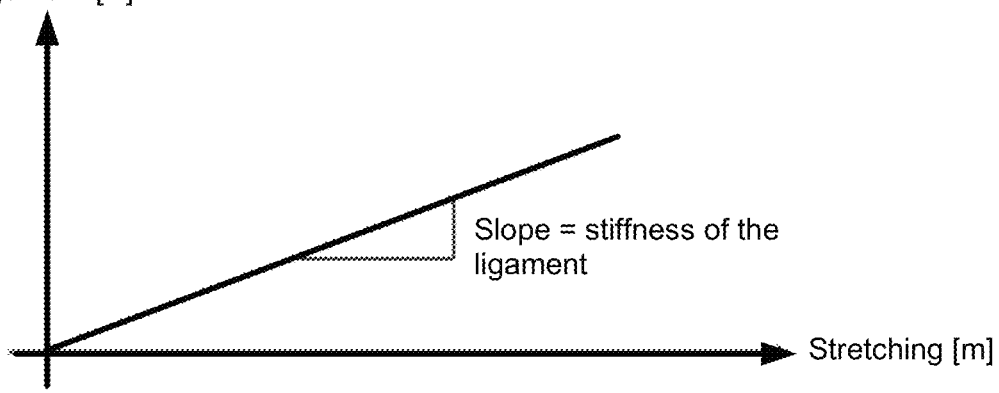
FIG. 10 illustrates a graph of force applied by the surgical robot system to the ligament as a function of stretch distance, and the stiffness of the ligament computed as the slope of the force to stretch in accordance with some embodiments of the present disclosure.

The robot system 100 may determine the ligaments mechanical properties by operating to repetitive cause different movements of the lower leg 622 to cause differing resultant forces on the knee while performing measurements of forces and/or torques. The ligaments mechanical properties, such as stiffness, can correspond to the force exerted by the ligament as a function of its stretching. FIG. 10 illustrates a graph of force applied by the robot system 100 to the ligament as a function of stretch distance, and the stiffness of the ligament computed as the slope of the force to stretch in accordance with some embodiments of the present disclosure.

In a corresponding operational embodiment, the at least one controller is further configured to determine stiffness of the ligaments based on a ratio between measurements of force applied by the ligaments and measurements of stretching of the ligaments while the joint is moved in the defined ROM, such as described with regard to FIG. 10.

The robot system 100 can determine ligaments balancing based on measurements obtained while specific movements of the knee are performed. As explained above, the robot system 100 may display the determined information to provide computer assistance for implant selection, implant placement, and/or assessment of estimated surgical procedure outcomes for the patient.

Figure 11:
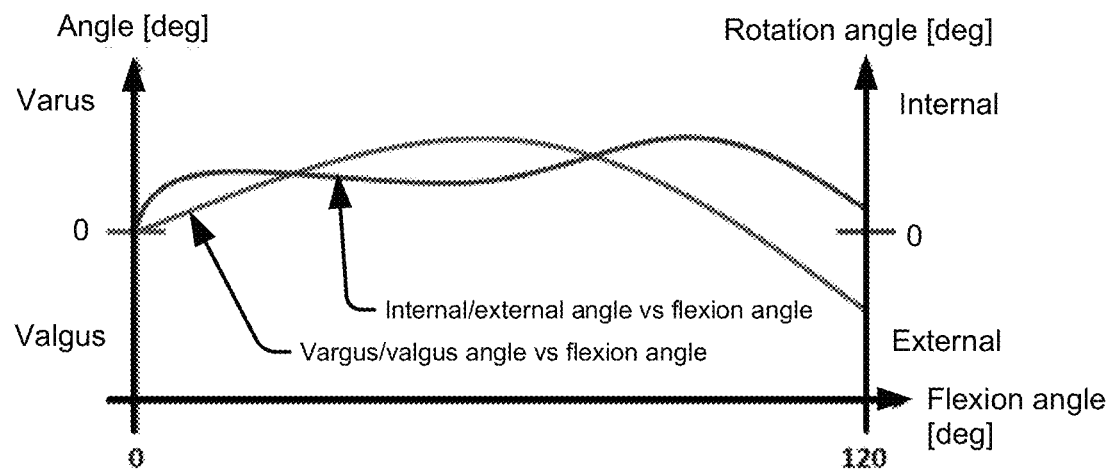
FIG. 11 illustrates example values which may be measured by the surgical robot system for a range of varus and valgus angles and a range of internal and external rotation angles, as a function of flexion performed on the knee in accordance with some embodiments of the present disclosure.

Various planning operations are now explained with reference to FIGS. 11 and 12. The robot system 100 may operate to move the lower leg 62 to cause the knee to move in a defined ROM while the robot system 100 applies defined, e.g., standardized, forces and/or torques to the knee. The measurements of force and/or torque by the robot system 100 can be used in a repeatable, e.g., predictable, way for planning, evaluation and comparison of procedures by different surgeons and different patients. As explained above, such repeatability is not available using prior manual surgeon-performed techniques due to the variability between different surgeons' presently perceived and previously remembered forces and movements, and due to the different subjective understandings of each of the surgeons.

For example, the robot system 100 can apply a progressive torque to the lower leg 62 to perform a complete flexion of the knee (e.g., according to the movements illustrated in FIG. 7), while measuring values for the varus and/or valgus angle and measuring values for the internal and/or external rotations in response to the forces. FIG. 11 illustrates example values which may be measured by the robot system 100 for a range of varus and valgus angles and a range of internal and external rotation angles, as a function of flexion performed on the knee in accordance with some embodiments of the present disclosure. During flexion, the robot system 100 may also measure sliding movements of the tibia with respect to the femur. In the context of FIG. 7, the sliding of the tibia with respect to the femur corresponds to the medial and/or lateral shift, the anterior and/or posterior shift and the inferior and/or superior shift.

Figure 12:
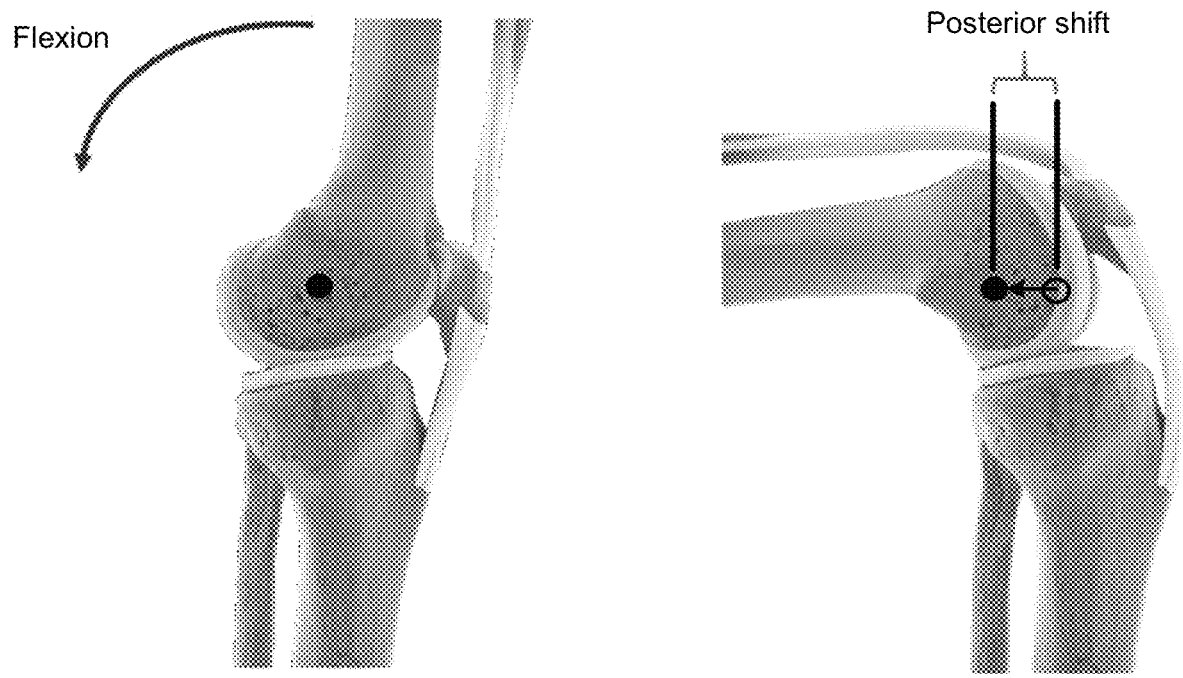
FIG. 12 illustrates an example of graph of posterior shift measured while performing flexion of a knee in accordance with some embodiments of the present disclosure.

FIG. 12 illustrates an example of graph of posterior shift measured while performing flexion of a knee in accordance with some embodiments of the present disclosure.

Figure 13:
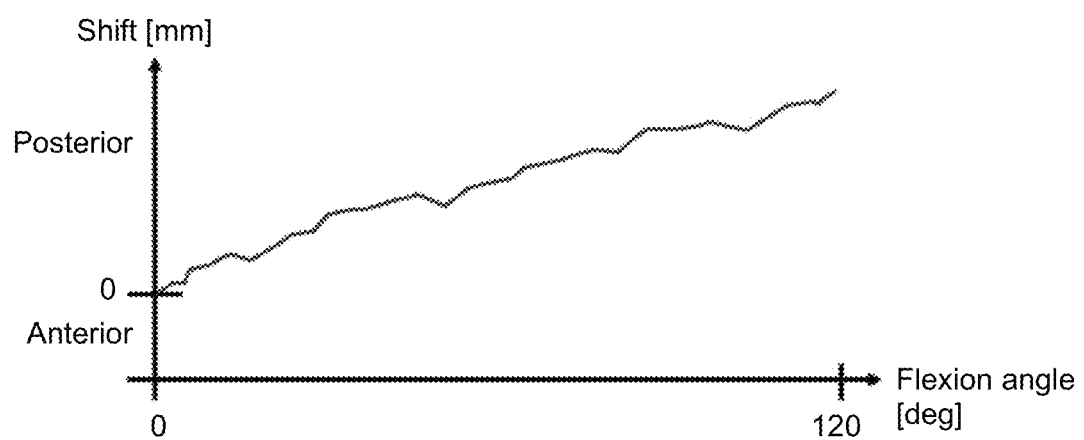
FIG. 13 illustrates an example graph of posterior shift as a function of flexion angle in accordance with some embodiments of the present disclosure.

The different shifts measured during a movement of the lower leg 62 may not be smooth because of friction. For example, while the head of the femoral bone is sliding on the head of the tibial bone the bones may get stuck because of the cartilage which is worn (due to the osteoarthritis) not being perfectly smooth. The friction forces can be measured by the sensors in the robotic arm 104, the end-effector 112, and/or the knee manipulation arm 60, and/or the friction forces may be determined by analyzing the positions and/or oscillations (e.g., of the measured friction force values) at various positions of the femur and tibia. The measured and/or determined friction forces can be displayed as additional useful information to the surgeon, such as for use in guiding osteophyte removal or informing about knee areas of particular concern due to osteoarthritis or cartilage degradation. FIG. 13 illustrates an example graph of posterior shift as a function of flexion angle in accordance with some embodiments of the present disclosure. The illustrated graph is not smooth, e.g., jerky, because of presence of osteophytes and/or osteoarthritis in the knee.

This information generated by the robot system 100 can be used by the robot system 100 to make recommendations to the surgeon and/or may be displayed to the surgeon to facilitate selection of a preferred patient treatment plan, selection of a preferred implant, determination of a preferred implant placement location, selection of an implant type, selection of an implant size, determination of a knee surgical cut plan, prediction of an outcome of a surgical surgery, etc., for the patient.

Example corresponding planning operations are explained with further reference to FIG. 14. The at least one controller may be further configured to perform a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque. The at least one controller can then process the pre-implant information to determine and output to an operator at least one of: a candidate position for the implant in the joint; a candidate size of the implant; and a candidate type of the implant.

The at least one controller may be further configured to access a knowledge database using the pre-implant information to determine the at least one of: the candidate position for the implant in the joint; the candidate size of the implant; and the candidate type of the implant. The knowledge database defines relationships between different sets of ligaments balancing values for a baseline joint and at least one of: different sets of preferred positions for an implant in the baseline joint; different sets of preferred implant sizes; and different sets of preferred implant types.

The at least one controller may be further configured to perform a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque. The at least one controller can then process the pre-implant information to determine and output to an operator at least one of a preferred joint surgical cut plan and a prediction characterizing an outcome of the preferred joint surgical cut plan.

Further operations are now explained which can be performed during the Free Knee Motion process to operate the robot system 100 to provide recommendations to the surgeon for cutting angles, implant size, implant type, etc.

The robot system 100 can operate to calculate distance between the articular surfaces of knee while performing movement of the knee in a ROM with successively applied varus and valgus stress to the knee and while tracking pose of both femur and tibia.

To apply valgus stress to the knee during movement in the ROM, the leg is moved by the robot system 100 in the knee's ROM, e.g., through the entire ROM, while applying valgus "force" to tension the Medial Collateral Ligament and thus ensure contact of the lateral condyle with the lateral tibial plateau in, e.g., throughout, the ROM. By tracking both tibia and femur location in space with the tracking camera 200 at the same time, the robot system 100 can calculate the distance with respect to flexion angle between the condylar surface and the tibial plateau surface on the medial side of the knee.

To apply varus stress to the knee during movement in the ROM, the leg is moved by the robot system 100 in the knee's ROM while applying varus "force" to tension the Lateral Collateral Ligament and thus ensure contact of the medial condyle with the medial tibial plateau in, e.g., throughout, the ROM. By tracking both tibia and femur location in space with the tracking camera 200 at the same time, the robot system 100 can calculate the distance with respect to flexion angle between the condylar surface and the tibial plateau surface on the lateral side of the knee.

It is noted that by having the robot system 100 apply the varus/valgus stress, the level of stress (forces and/or torques) applied to the knee joint can be specifically control and, thereby, increase repeatability of the acquired data.

As soon as distances between articular surfaces have been acquired, planning program module executed by the at least one controller uses the distances as input data and selects the most appropriate combination of implants sizes as well as implants positions and orientations with respect to the bone in order to optimize and reproduce as close as possible the measured distances between articular surfaces. Once the optimal position and orientation of both implants with respect to their respective bone has been determined by the planning program module, the corresponding resections planes and angles can be calculated accordingly (i.e., by knowing the implant's geometries and fitting rules).

After that, surgeon can still modify implants positions and orientations, based for example on effective calculated flexion and extension resection gaps.

The robot system 100 can also operate to select an appropriate implant or implant position based on ligament flexibility. The measurement of gaps between articular surfaces, as discussed above, is an indirect measurement of the ligament stiffness. Indeed, the more the ligaments "flexible" (compliant) are, the more distance that is consequently measured. As the ligaments can be considered as anatomical elastics, by determining the length of these elastics, attachment points on bones and their respective stiffness rate (the elongation vs applied force), the robot system 100 can then determine optimized implant position and orientation to ensure that ligaments are under tension and/or lax in certain position of the knee (in flexion, mid-flexion or extension).

The robot system 100 can also operate to access the knowledge database for planning. Based on the definition of a specific controlled leg movement (combination of ROM movement and specific movement for ligaments assessment, as described above) that could be performed with the robot arm 104, with control of monitoring of forces and torques applied to knee joint throughout the ROM. Based on the measurements of reaction forces (by means of the force and/or torque sensor apparatus, e.g. of the robot arm 104) as well as tracked position of both bones using the tracking camera 200, the robot system 100 (i.e., the at least one controller thereof) can determine the full biomechanical behavior (external/internal rotation, varus/valgus angles, posterior shift, etc.) of the knee joint and specifically adjust implant placement based on this assessment.

Figure 15:
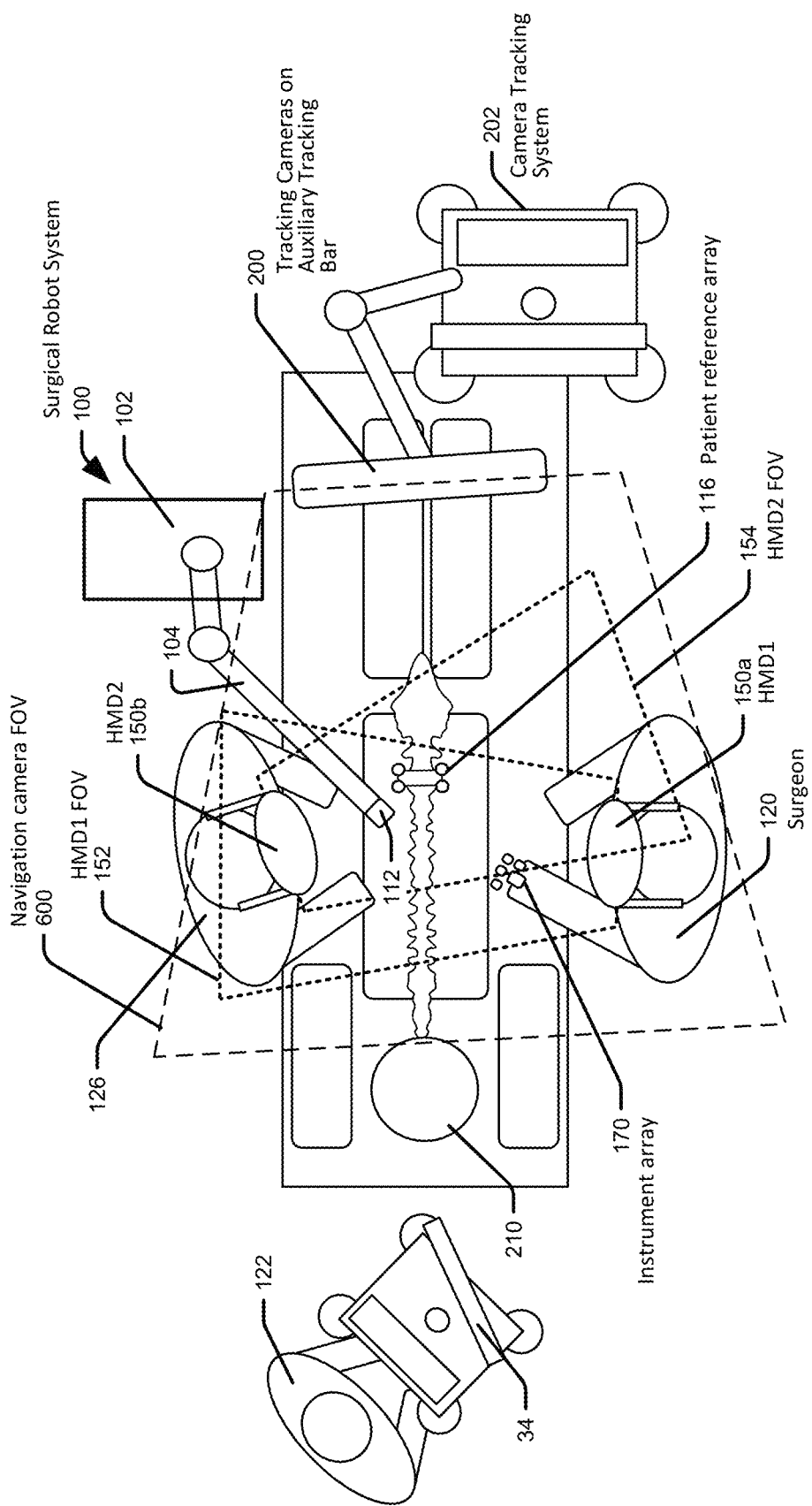
FIG. 15 is an overhead view of a personnel wearing extended reality (XR) headsets during a surgical procedure in a surgical room that includes a camera tracking system for navigated surgery and a surgical robot system for robotic assistance and configured in accordance with some embodiments.

Example Surgical Room Equipment Layout and Operation:

FIG. 15 is an overhead view of a personnel wearing extended reality (XR) headsets 150a and 150b during a surgical procedure in a surgical room that includes a camera tracking system 202 for navigated surgery and the robot system 100 for robotic assistance and configured in accordance with some embodiments.

Referring to FIG. 15, the robot system 100 may include, for example, a surgical robot 102, one or more robotic arms 104, a display 110, an end-effector 112, for example, configured to attach to a joint manipulation arm, and an end-effector reference array which can include one or more tracking markers. The robot system 100 may include a patient reference array 116 with a plurality of tracking markers, which is adapted to be secured directly to the patient 210 (e.g., to a bone of the patient 210). Another reference array 170 is attached or formed on a joint manipulation arm, etc. The robot system 100 may also utilize a tracking camera 200, for example, positioned on the camera tracking system 202. The camera tracking system 202 can have any suitable configuration to move, orient, and support the tracking camera 200 in a desired position, and may contain a computer operable to track pose of reference arrays.

The tracking camera 200 may include any suitable camera or cameras, such as one or more infrared cameras (e.g., bifocal or stereophotogrammetric cameras), able to identify, for example, active and passive tracking markers for various reference arrays attached as the patient 210 (patient reference array), end-effector 112 (end-effector reference array), joint manipulation arm, extended reality (XR) headset(s) 150a-150b worn by a surgeon 120 and/or a surgical assistant 126, etc. in a given measurement volume viewable from the perspective of the tracking camera 200. The tracking camera 200 may track markers 170 attached to a joint manipulation arm manipulated by a user (surgeon) and/or the robot system. The tracking camera 200 may scan the given measurement volume and detect the light that is emitted or reflected from the reference arrays in order to identify and determine poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking camera 200 or other suitable device.

The XR headsets 150a and 150b (also referred to as an XR headset 150) may each include tracking cameras that can track poses of reference arrays within their camera field-of-views (FOVs) 152 and 154, respectively. Accordingly, as illustrated in FIG. 15, the poses of reference arrays attached to various objects can be tracked while in the FOVs 152 and 154 of the XR headsets 150a and 150b and/or a FOV 600 of the tracking cameras 200.

An XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. Thus, the term XR headset can referred to as an AR headset or a VR headset.

FIG. 1 illustrates a potential configuration for the placement of the camera tracking system 202 and the surgical robot system 100 in an operating room environment. Computer-aided navigated surgery can be provided by the camera tracking system controlling the XR headsets 150a and 150b to display surgical procedure navigation information. The surgical robot system 100 in optional during computer-aided navigated surgery.

The camera tracking system 202 may use tracking information and other information from multiple XR headsets 150a and 150b such as inertial tracking information and optical tracking information as well as (optional) microphone information. The XR headsets 150a and 150b operate to display visual information and play-out audio information to the wearer. This information can be from local sources (e.g., the surgical robot 102 and/or other medical), remote sources (e.g., patient medical image server), and/or other electronic equipment. The XR headsets 150a and 150b track apparatus such as instruments, patient references and end-effectors in 6 degrees-of-freedom (6DOF), and may track the hands of the wearer. The XR headsets 150a and 150b may also operate to track hand poses and gestures to enable gesture based interactions with "virtual" buttons and interfaces displayed through the XR headsets 150a and 150b and can also interpret hand or finger pointing or gesturing as various defined commands. Additionally, the XR headsets 150a and 150b may have a 1-10× magnification digital color camera sensor called a digital loupe.

An "outside-in" machine vision navigation bar (tracking cameras 200) may track pose of the joint manipulation arm using monochrome and/or color camera(s). The machine vision navigation bar generally has a more stable view of the environment because it does not move as often or as quickly as the XR headsets 150a and 150b tend to move while positioned on wearers' heads. The patient reference array 116 is generally rigidly attached to the patient with stable pitch and roll relative to gravity. This local rigid patient reference 116 can serve as a common reference for reference frames relative to other tracked arrays, such as a reference array on the end-effector 112, instrument reference array 170, and reference arrays on the XR headsets 150a and 150b.

In some embodiments, one or more of the XR headsets 150a and 150b are minimalistic XR headsets that display local or remote information but include fewer sensors and are therefore more lightweight.

The robot system 100 may be positioned near or next to patient 210. The tracking camera 200 may be separated from the robot system 100 and positioned at the foot of patient 210. This location allows the tracking camera 200 to have a direct visual line of sight to the surgical field 208. It is contemplated that the robot system 100 and the tracking camera 200 will be located at any suitable position. In the configuration shown, the surgeon 120 may be positioned across from the robot 102, but is still able to manipulate the end-effector 112 (and joint manipulation arm) and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200. The anesthesiologist 122 can operate anesthesia equipment which can include a display 34.

With respect to the other components of the robot 102, the display 110 can be attached to the surgical robot 102 and in other example embodiments, display 110 can be detached from surgical robot 102, either within a surgical room with the surgical robot 102, or in a remote location. End-effector 112 may be coupled to the robotic arm 104 and controlled by at least one motor. In example embodiments, end-effector 112 can be connectable to a joint manipulation arm and, alternatively, a guide tube 114, which is able to receive and orient a surgical instrument, tool, or implant 608 used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, joint manipulation arms, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is operable to control the translation and orientation of the end-effector 112. The robot 102 is operable to move end-effector 112 under computer control along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively computer controlled). In some example embodiments, selective control of the translation and orientation of end-effector 112 can permit performance of medical procedures with significantly improved accuracy compared to conventional robots that utilize, for example, a six degree of freedom robotic arm comprising only rotational axes. For example, the surgical robot system 100 may be used to operate on patient 210, and robotic arm 104 can be positioned above the body of patient 210, with end-effector 112 selectively angled relative to the z-axis toward the body of patient 210.

In some example embodiments, the XR headsets 150a and 150b can be controlled to dynamically display an updated graphical indication of the pose of the surgical instrument so that the user can be aware of the pose of the surgical instrument at all times during the procedure.

As used herein, the term "pose" refers to the position and/or the rotational angle of one object (e.g., dynamic reference array, end-effector, surgical instrument, anatomical structure, etc.) relative to another object and/or to a defined coordinate system. A pose may therefore be defined based on only the multidimensional position of one object relative to another object and/or relative to a defined coordinate system, based on only the multidimensional rotational angles of the object relative to another object and/or to a defined coordinate system, or based on a combination of the multidimensional position and the multidimensional rotational angles. The term "pose" therefore is used to refer to position, rotational angle, or combination thereof.

In some further embodiments, surgical robot 102 can be configured to correct the path of the joint manipulation arm being moved by the surgeon with guidance by the robotic arm 104. In some example embodiments, surgical robot 102 can be configured to permit stoppage, modification, and/or manual control of the movement of end-effector 112 and/or the joint manipulation arm. Thus, in use, in example embodiments, a surgeon or other user can operate the system 100, and has the option to stop, modify, or manually control the autonomous movement of end-effector 112 and/or the joint manipulation arm.

Reference arrays can be formed on or connected to robotic arm 104, end-effector 112, joint manipulation arm 60, patient 210, and/or the surgical instrument to track poses in 6 degree-of-freedom (e.g., position along 3 orthogonal axes and rotation about the axes). In example embodiments, a reference array including a plurality of tracking markers can be provided thereon (e.g., formed-on or connected-to) to an outer surface of the robot 102, such as on robot 102, on robotic arm 104, and/or on the end-effector 112. A patient reference array including one or more tracking markers can further be provided on the patient 210 (e.g., formed-on or connected-to). An instrument reference array including one or more tracking markers can be provided on surgical instruments (e.g., a screwdriver, dilator, implant inserter, or the like). The reference arrays enable each of the marked objects (e.g., the end-effector 112, the patient 210, and the surgical instruments) to be tracked by the tracking camera 200, and the tracked poses can be used to provide navigation guidance to a surgical procedure and/or used to control movement of the surgical robot 102 for guiding the end-effector 112, joint manipulation arm, and/or an instrument.

Figure 16:
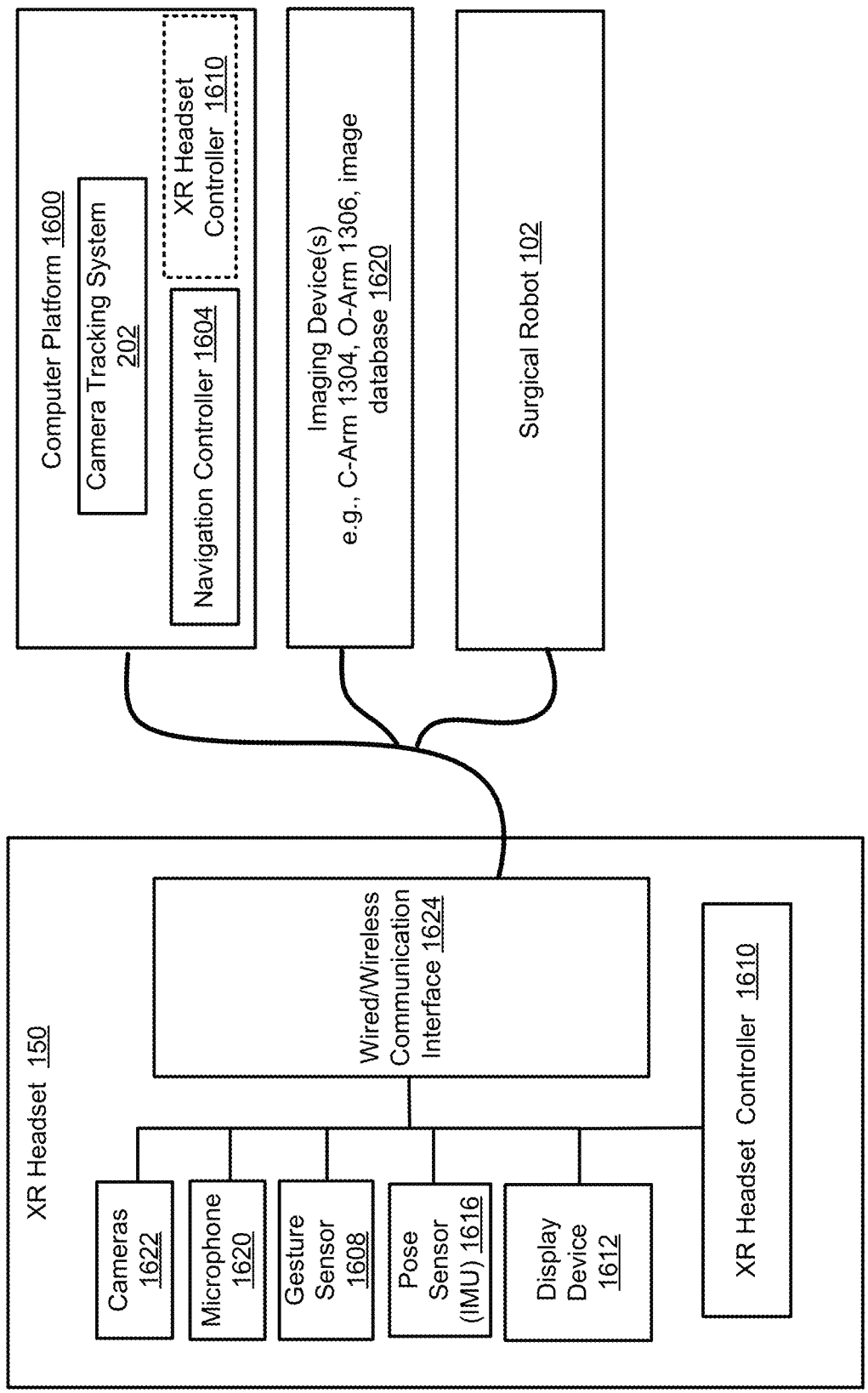
FIG. 16 illustrates a block diagram of a surgical robot system that includes an XR headset, a computer platform, and a camera tracking system component which are operative in accordance with some embodiments.

Example Surgical System:

FIG. 16 illustrates a block diagram of a surgical robot system that includes an XR headset 150, a computer platform 1600, imaging devices, and a surgical robot 102 which are configured to operate in accordance with various embodiments.

The imaging devices may include a C-arm imaging device 1304, an O-arm imaging device 1306, and/or a patient image database 1620. The XR headset 150 provides an improved human interface for performing navigated surgical procedures. The XR headset 150 can be configured to provide functionalities, e.g., via the computer platform 1600, that include without limitation any one or more of: identification of hand gesture based commands, display XR graphical objects on a display device 1612. The display device 1612 may a video projector, flat panel display, etc. The user can view the XR graphical objects as an overlay anchored to particular real-world objects viewed through a see-through display screen. The XR headset 150 may additionally or alternatively be configured to display on the display device 1612 video streams from cameras mounted to one or more XR headsets 150 and other cameras.

Electrical components of the XR headset 150 can include a plurality of cameras 1622, a microphone 1620, a gesture sensor 1618, a pose sensor (e.g., inertial measurement unit (IMU)) 1616, the display device 1612, and a wireless/wired communication interface 1624. The cameras 1622 of the XR headset 150 may be visible light capturing cameras, near infrared capturing cameras, or a combination of both.

The cameras 1622 may be configured to operate as the gesture sensor 1618 by tracking for identification user hand gestures performed within the field of view of the camera(s) 1622. Alternatively the gesture sensor 1618 may be a proximity sensor and/or a touch sensor that senses hand gestures performed proximately to the gesture sensor 1618 and/or senses physical contact, e.g. tapping on the sensor 1618 or its enclosure. The pose sensor 1616, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes a camera tracking system 202 which may be part of a computer platform 1600 that can also provide functionality of a navigation controller 1604 and/or of a XR headset controller 1610. The surgical system may include the imaging devices and/or a surgical robot 102. The navigation controller 1604 can be configured to provide visual navigation guidance to an operator for moving and positioning a joint manipulation arm during a joint ligaments balancing procedure and/or moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 202. The navigation controller 1604 may be further configured to generate navigation information based on a target pose for a surgical tool, a pose of the anatomical structure, and a pose of the surgical tool and/or an end-effector of the surgical robot 102, where the steering information is used to display information through the XR headset 150 to indicate where the surgical tool and/or the end-effector of the surgical robot 102 should be moved to perform the surgical plan.

The electrical components of the XR headset 150 can be operatively connected to the electrical components of the computer platform 1600 through a wired/wireless interface 1624. The electrical components of the XR headset 150 may be operatively connected, e.g., through the computer platform 1600 or directly connected, to various imaging devices, e.g., the C-arm imaging device 1304, the I/O-arm imaging device 1306, the patient image database 1620, and/or to other medical equipment through the wired/wireless interface 1624.

The surgical system further includes at least one XR headset controller 1610 that may reside in the XR headset 150, the computer platform 1600, and/or in another system component connected via wired cables and/or wireless communication links. Various functionality is provided by software executed by the XR headset controller 1610. The XR headset controller 1610 is configured to receive information from the camera tracking system 202 and the navigation controller 1604, and to generate an XR image based on the information for display on the display device 1612.

The XR headset controller 1610 can be configured to operationally process signaling from the cameras 1622, the microphone 1620, and/or the pose sensor 1616, and is connected to display XR images on the display device 1612 for user viewing. Thus, the XR headset controller 1610 illustrated as a circuit block within the XR headset 150 is to be understood as being operationally connected to other illustrated components of the XR headset 150 but not necessarily residing within a common housing or being otherwise transportable by the user. For example, the XR headset controller 1610 may reside within the computer platform 1600 which, in turn, may reside within a housing of the surgical robot 102, the camera tracking system 202, etc.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A method by a surgical robot system including a surgical robot with a robot arm connected to move a joint manipulation arm to apply force and/or torque to a joint connecting an appendage of a patient, the method comprising:
   obtaining, from a force and/or torque sensor apparatus, a feedback signal providing an indication of an amount of force and/or torque that is being applied to the robot arm and/or the joint manipulation arm;
   determining ligaments balancing at the joint based on a plurality of measurements of the feedback signal, and to output information characterizing the ligaments balancing; and
   performing the determination of ligaments balancing to output the information characterizing ligaments balancing at the joint, based on repeated measurements of the feedback signal indication of the amount of force and/or torque while the joint is moved in a defined range of motion (ROM).

2. The method of claim 1, further comprising:
   performing a pre-implant determination of ligaments balancing to output pre-implant information characterizing ligaments balancing at the joint before surgical placement of an implant in the joint; and
   performing a post-implant determination of ligaments balancing to output post-implant information characterizing ligaments balancing at the joint after surgical placement of the implant in the joint.

3. The method of claim 2, further comprising:
   determining stiffness of the ligaments based on a ratio between measurements of force applied by the ligaments and measurements of stretching of the ligaments while the joint is moved in the defined ROM.

4. The method of claim 2, further comprising:
   controlling at least one motor of the surgical robot to move the robot arm to cause the joint to move in the defined ROM without lateral forces being applied to the knee and while performing a first set of measurements of the feedback signal indicating the amount of force and/or torque that is being applied to the joint;
   controlling the at least one motor to move the robot arm and cause the joint in the defined ROM with defined lateral forces being applied to the knee and while performing a second set of measurements of the feedback signal indicating the amount of force and/or torque that is being applied to the joint; and
   determining the ligaments balancing based on a combination of the first and second sets of measurements.

5. The method of claim 2, further comprising:
   performing a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque; and
   processing the pre-implant information to determine and output to an operator at least one of: a candidate position for the implant in the joint; a candidate size of the implant; and a candidate type of the implant.

6. The method of claim 5, further comprising:
   accessing a knowledge database using the pre-implant information to determine the at least one of: the candidate position for the implant in the joint; the candidate size of the implant; and the candidate type of the implant, wherein the knowledge database defines relationships between different sets of ligaments balancing values for a baseline joint and at least one of: different sets of preferred positions for an implant in the baseline joint; different sets of preferred implant sizes; and different sets of preferred implant types.

7. The method of claim 2, further comprising:
   performing a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque; and
   processing the pre-implant information to determine and output to an operator at least one of a preferred joint surgical cut plan and a prediction characterizing an outcome of the preferred joint surgical cut plan.

8. A method by a surgical robot system including a surgical robot with a robot arm connected to move a joint manipulation arm to apply force and/or torque to a joint connecting an appendage of a patient, the method comprising:
   obtaining, from a force and/or torque sensor apparatus, a feedback signal providing an indication of an amount of force and/or torque that is being applied to the robot arm and/or the joint manipulation arm; and
   determining ligaments balancing at the joint based on a plurality of measurements of the feedback signal, and to output information characterizing the ligaments balancing,
   wherein the surgical robotic system autonomously positions the joint manipulation arm at an optimal position based on the plurality of measurements of the feedback signal.

9. The method of claim 8, further comprising:
   performing a pre-implant determination of ligaments balancing to output pre-implant information characterizing ligaments balancing at the joint before surgical placement of an implant in the joint; and
   performing a post-implant determination of ligaments balancing to output post-implant information characterizing ligaments balancing at the joint after surgical placement of the implant in the joint.

10. The method of claim 8, further comprising:
performing the determination of ligaments balancing to output the information characterizing ligaments balancing at the joint, based on repeated measurements of the feedback signal indication of the amount of force and/or torque while the joint is moved in a defined range of motion (ROM).

11. The method of claim 10, further comprising:
determining stiffness of the ligaments based on a ratio between measurements of force applied by the ligaments and measurements of stretching of the ligaments while the joint is moved in the defined ROM.

12. The method of claim 10, further comprising:
controlling at least one motor of the surgical robot to move the robot arm to cause the joint to move in the defined ROM without lateral forces being applied to the knee and while performing a first set of measurements of the feedback signal indicating the amount of force and/or torque that is being applied to the joint;
controlling the at least one motor to move the robot arm and cause the joint in the defined ROM with defined lateral forces being applied to the knee and while performing a second set of measurements of the feedback signal indicating the amount of force and/or torque that is being applied to the joint; and
determining the ligaments balancing based on a combination of the first and second sets of measurements.

13. The method of claim 10, further comprising:
performing a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque; and
processing the pre-implant information to determine and output to an operator at least one of: a candidate position for the implant in the joint; a candidate size of the implant; and a candidate type of the implant.

14. The method of claim 13, further comprising:
accessing a knowledge database using the pre-implant information to determine the at least one of: the candidate position for the implant in the joint; the candidate size of the implant; and the candidate type of the implant, wherein the knowledge database defines relationships between different sets of ligaments balancing values for a baseline joint and at least one of: different sets of preferred positions for an implant in the baseline joint; different sets of preferred implant sizes; and different sets of preferred implant types.

15. The method of claim 10, further comprising:
performing a pre-implant determination of ligaments balancing to output pre-implant information characterizing ligaments balancing at the joint before surgical placement of an implant in the joint, based on movement of the joint in the defined ROM while measuring the feedback signal indication of the amount of force and/or torque; and
processing the pre-implant information to determine and output to an operator at least one of a preferred joint surgical cut plan and a prediction characterizing an outcome of the preferred joint surgical cut plan.

* * * * *